(12) United States Patent
Kuo

(10) Patent No.: US 11,808,694 B2
(45) Date of Patent: Nov. 7, 2023

(54) GAS CONCENTRATION MEASUREMENT SYSTEM AND AIRWAY ADAPTER THEREOF

(71) Applicant: COMDEK INDUSTRIAL CORPORATION, New Taipei (TW)

(72) Inventor: Yi-Sung Kuo, New Taipei (TW)

(73) Assignee: COMDEK INDUSTRIAL CORPORATION, New Taipei (TW)

( * ) Notice: Subject to any disclaimer, the term of this patent is extended or adjusted under 35 U.S.C. 154(b) by 431 days.

(21) Appl. No.: 17/246,811

(22) Filed: May 3, 2021

(65) Prior Publication Data

US 2022/0187192 A1    Jun. 16, 2022

(30) Foreign Application Priority Data

Dec. 11, 2020  (TW) ................................ 109143752

(51) Int. Cl.

| | | |
|---|---|---|
| *G01N 21/05* | (2006.01) | |
| *G01N 21/85* | (2006.01) | |
| *G01N 33/497* | (2006.01) | |
| *G01N 21/3504* | (2014.01) | |
| *G01N 21/61* | (2006.01) | |

(52) U.S. Cl.
CPC ......... *G01N 21/05* (2013.01); *G01N 21/3504* (2013.01); *G01N 21/85* (2013.01); *G01N 33/497* (2013.01); *G01N 21/61* (2013.01); *G01N 2021/052* (2013.01); *G01N 2021/8578* (2013.01)

(58) Field of Classification Search
CPC .... G01N 21/05; G01N 21/3504; G01N 21/85; G01N 33/497; G01N 21/61; G01N 2021/052; G01N 2021/8578
See application file for complete search history.

(56) References Cited

U.S. PATENT DOCUMENTS

| | | | |
|---|---|---|---|
| 9,521,963 B2 * | 12/2016 | Esposito | ................ A61B 5/061 |
| 2006/0009707 A1 | 1/2006 | Daniels et al. | |
| 2015/0241359 A1 * | 8/2015 | Haveri | ................ G01N 33/497 |
| | | | 250/339.02 |

FOREIGN PATENT DOCUMENTS

TW            201700901 A     1/2017

* cited by examiner

*Primary Examiner* — Benjamin R Schmitt

(74) *Attorney, Agent, or Firm* — Li & Cai Intellectual Property (USA) Office

(57) ABSTRACT

A gas concentration measurement system and an airway adapter thereof are provided. The gas concentration measurement system includes the airway adapter and a gas concentration detection device including a main body. The main body includes an accommodating passageway, a check unit, a transmitter unit and a receiver unit. The airway adapter includes an inlet section, a detection section, an identification part and an outlet section. The detection section includes a light entering detection window and a light exiting detection window that are integrally formed. The identification part has an identification chip disposed therein. When the airway adapter is mated with the accommodating passageway of the gas concentration detection device along an axis of the airway adapter, the identification chip of the identification part is read to check whether or not the airway adapter is matched with the gas concentration detection device.

16 Claims, 9 Drawing Sheets

GAS CONCENTRATION MEASUREMENT SYSTEM AND AIRWAY ADAPTER THEREOF

CROSS-REFERENCE TO RELATED PATENT APPLICATION

This application claims the benefit of priority to Taiwan Patent Application No. 109143752, filed on Dec. 11, 2020. The entire content of the above identified application is incorporated herein by reference.

Some references, which may include patents, patent applications and various publications, may be cited and discussed in the description of this disclosure. The citation and/or discussion of such references is provided merely to clarify the description of the present disclosure and is not an admission that any such reference is "prior art" to the disclosure described herein. All references cited and discussed in this specification are incorporated herein by reference in their entireties and to the same extent as if each reference was individually incorporated by reference.

FIELD OF THE DISCLOSURE

The present disclosure relates to a gas concentration measurement system including a gas concentration detection device and an airway adapter, and more particularly to a mainstream end tidal $CO_2$ concentration monitoring instrument.

BACKGROUND OF THE DISCLOSURE

In clinical and other medical monitoring, end tidal $CO_2$ concentration and respiratory flow monitoring of a patient (test subject) is important, and can provide important guidance for disease diagnosis and clinical monitoring. The end tidal $CO_2$ concentration monitoring can include a mainstream method and a sidestream method. The mainstream method is a direct measurement monitoring method, whereas the sidestream method is a measurement method through extracting an exhaled air.

Through performing monitoring directly on a piping adapter of the patient in the mainstream method, problems such as delay and distortion are prevented. Currently, the mainstream $CO_2$ monitoring technology has a fast response and a stable performance, but is easily susceptible to many factors. For example, water vapor from breathing of the patient will absorb infrared light which affects measurement accuracy. Moreover, a measurement adapter pipe of a conventional mainstream $CO_2$ monitoring device is usually inserted into a measurement host from an outer side in a direction perpendicular to an airflow. However, the measurement adapter pipe of such a monitoring device is partially exposed and is susceptible to an external light.

SUMMARY OF THE DISCLOSURE

In response to the above-referenced technical inadequacies, the present disclosure provides a gas concentration measurement system and an airway adapter thereof. The airway adapter can be completely surrounded and covered, so as to prevent possible light interference and to improve measurement accuracy.

In one aspect, the present disclosure provides a gas concentration measurement system, which includes a gas concentration detection device and an airway adapter. The gas concentration detection device includes a main body. The main body includes an accommodating passageway, a check unit, a transmitter unit and a receiver unit. The accommodating passageway is in a cylindrical shape and passes through the main body to form a circular inlet and a circular outlet. The transmitter unit and the receiver unit are oppositely disposed on two sides of the accommodating passageway. The check unit is disposed between the transmitter unit and the receiver unit. The check unit includes a plurality of check terminals, and the plurality of check terminals are exposed in the accommodating passageway. The airway adapter includes an inlet section, a detection section, an identification part and an outlet section. The detection section is integrally connected between the inlet section and the outlet section. The detection section includes a light entering detection window and a light exiting detection window that are integrally formed. The light entering detection window and the light exiting detection window are oppositely arranged on two sides of the detection section. The identification part is disposed on one side of the detection section. The identification part has an identification chip disposed therein. An outer diameter of the inlet section is greater than an outer diameter of the outlet section. When the airway adapter is mated with the accommodating passageway of the gas concentration detection device along an axis of the airway adapter, the plurality of check terminals abut the identification chip of the identification part to check whether or not the airway passageway is matched with the gas concentration detection device. The outer diameter of the outlet section is equal to a diameter of the accommodating passageway and is in tight contact with the circular outlet of the accommodating passageway. One end of the inlet section abuts and covers the circular outlet of the accommodating passageway.

In another aspect, the present disclosure provides an airway adapter suitable for a gas concentration detection device of a gas concentration measurement system. The gas concentration detection device includes a main body. The main body includes an accommodating passageway, a check unit, a transmitter unit and a receiver unit. The transmitter unit and the receiver unit are oppositely disposed on two sides of the accommodating passageway. The check unit is disposed between the transmitter unit and the receiver unit. The check unit includes a plurality of check terminals. The plurality of check terminals are exposed in the accommodating passageway. The accommodating passageway is in a cylindrical shape and passes through the main body to form a circular inlet and a circular outlet. The airway adapter includes an inlet section, a detection section, an identification part and an outlet section. The detection section is integrally connected between the inlet section and the outlet section. The detection section includes a light entering detection window and a light exiting detection window that are integrally formed. The light entering detection window and the light exiting detection window are oppositely arranged on two sides of the detection section. The identification part is disposed on one side of the detection section. The identification part has an identification chip disposed therein. An outer diameter of the inlet section is greater than an outer diameter of the outlet section. When the airway adapter is mated with the accommodating passageway of the gas concentration detection device along an axis of the airway adapter, the plurality of check terminals abut the identification chip of the identification part to check whether or not the airway passageway is matched with the gas concentration detection device. The outer diameter of the outlet section is substantially equal to a diameter of the accommodating passageway and is in tight contact with the circular outlet of the accommodating passageway. One end of the inlet section abuts and covers the circular outlet of the accommodating passageway.

Therefore, one of the beneficial effects of the present disclosure is that the gas concentration measurement system provided by the present disclosure can be mated with the accommodating passageway of the gas concentration detection device along the axis of the airway adapter, so that the detection section of the airway adapter can be completely surrounded and covered, thereby preventing the possible light interference and improving the measurement accuracy. In addition, the gas concentration detection device includes the check unit, and the airway adapter includes the identification part. The plurality of check terminals of the check unit abut the identification chip of the identification part to check whether or not the airway adapter is matched with the gas concentration detection device.

These and other aspects of the present disclosure will become apparent from the following description of the embodiment taken in conjunction with the following drawings and their captions, although variations and modifications therein may be affected without departing from the spirit and scope of the novel concepts of the disclosure.

BRIEF DESCRIPTION OF THE DRAWINGS

The described embodiments may be better understood by reference to the following description and the accompanying drawings, in which.

DETAILED DESCRIPTION OF THE EXEMPLARY EMBODIMENTS

Figure 1:
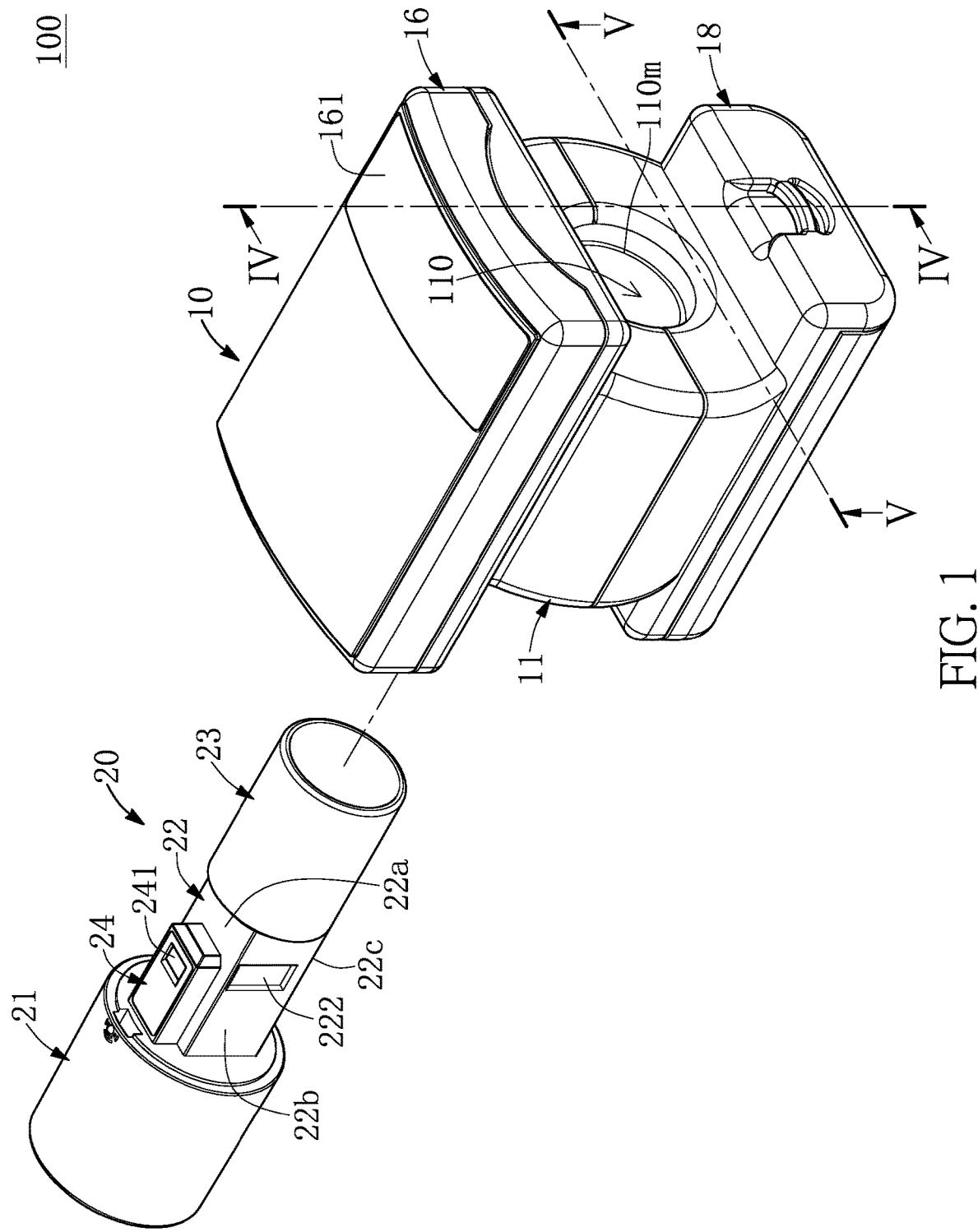
FIG. 1 is a perspective exploded view of a gas concentration measurement system according to the present disclosure.

The present disclosure is more particularly described in the following examples that are intended as illustrative only since numerous modifications and variations therein will be apparent to those skilled in the art. Like numbers in the drawings indicate like components throughout the views. As used in the description herein and throughout the claims that follow, unless the context clearly dictates otherwise, the meaning of "a", "an", and "the" includes plural reference, and the meaning of "in" includes "in" and "on". Titles or subtitles can be used herein for the convenience of a reader, which shall have no influence on the scope of the present disclosure.

The terms used herein generally have their ordinary meanings in the art. In the case of conflict, the present document, including any definitions given herein, will prevail. The same thing can be expressed in more than one way. Alternative language and synonyms can be used for any term(s) discussed herein, and no special significance is to be placed upon whether a term is elaborated or discussed herein. A recital of one or more synonyms does not exclude the use of other synonyms. The use of examples anywhere in this specification including examples of any terms is illustrative only, and in no way limits the scope and meaning of the present disclosure or of any exemplified term. Likewise, the present disclosure is not limited to various embodiments given herein. Numbering terms such as "first", "second" or "third" can be used to describe various components, signals or the like, which are for distinguishing one component/signal from another one only, and are not intended to, nor should be construed to impose any substantive limitations on the components, signals or the like.

Referring to FIG. 1 to FIG. 5, one embodiment of the present disclosure provides a gas concentration measurement system 100, which includes a gas concentration detection device 10 and an airway adapter 20. The airway adapter 20 is mated with the gas concentration detection device 10 along an axis of the airway adapter 20. One end of the airway adapter 20 is used to receive a gas exhaled by a test subject, and another end of the airway adapter 20 is used to discharge the gas outward. The gas concentration measurement system 100 of the present disclosure is suitable for a mainstream $CO_2$ detector for end tidal $CO_2$ ($EtCO_2$) monitoring. However, the present disclosure is not limited thereto.

Figure 2:
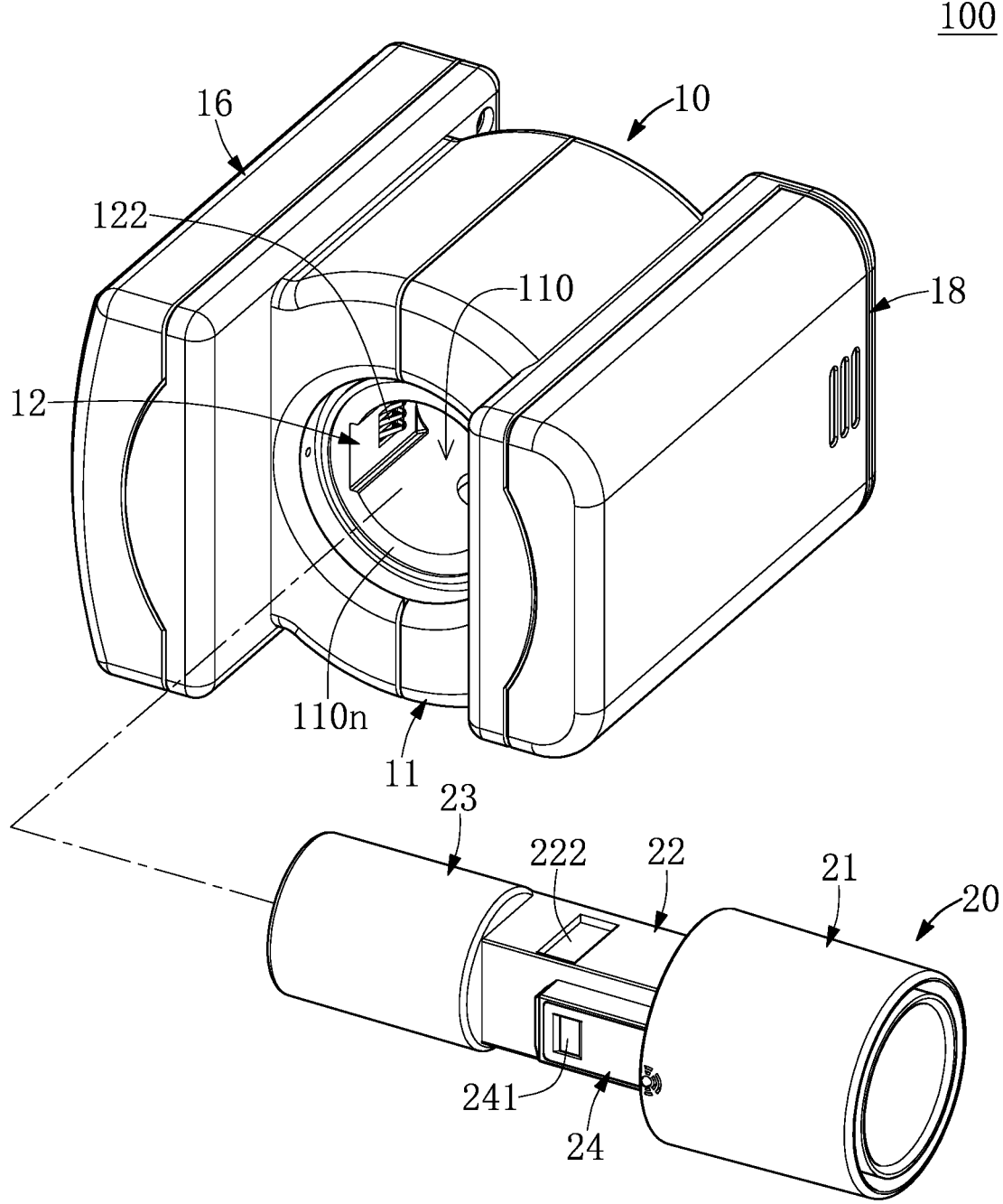
FIG. 2 is another perspective exploded view of the gas concentration measurement system according to the present disclosure.

The gas concentration detection device 10 includes a main body 11, an operation module 16 and a power supply module 18. The operation module 16 and the power supply module 18 are disposed on two sides of the main body 11, respectively. The main body 11 includes an accommodating passageway 110, a check unit 12, a transmitter unit 13 and a receiver unit 14. The accommodating passageway 110 in the present embodiment is in a cylindrical shape and passes through the main body 11 to form a circular inlet 110n (as shown in FIG. 2) and a circular outlet 110m (as shown in FIG. 1). The transmitter unit 13 and the receiver unit 14 are oppositely disposed on two sides of the accommodating passageway 110. The check unit 12 is disposed between the transmitter unit 13 and the receiver unit 14. The check unit 12 includes a plurality of check terminals 122, and the plurality of check terminals 122 are exposed in the accommodating passageway 110.

Figure 4:
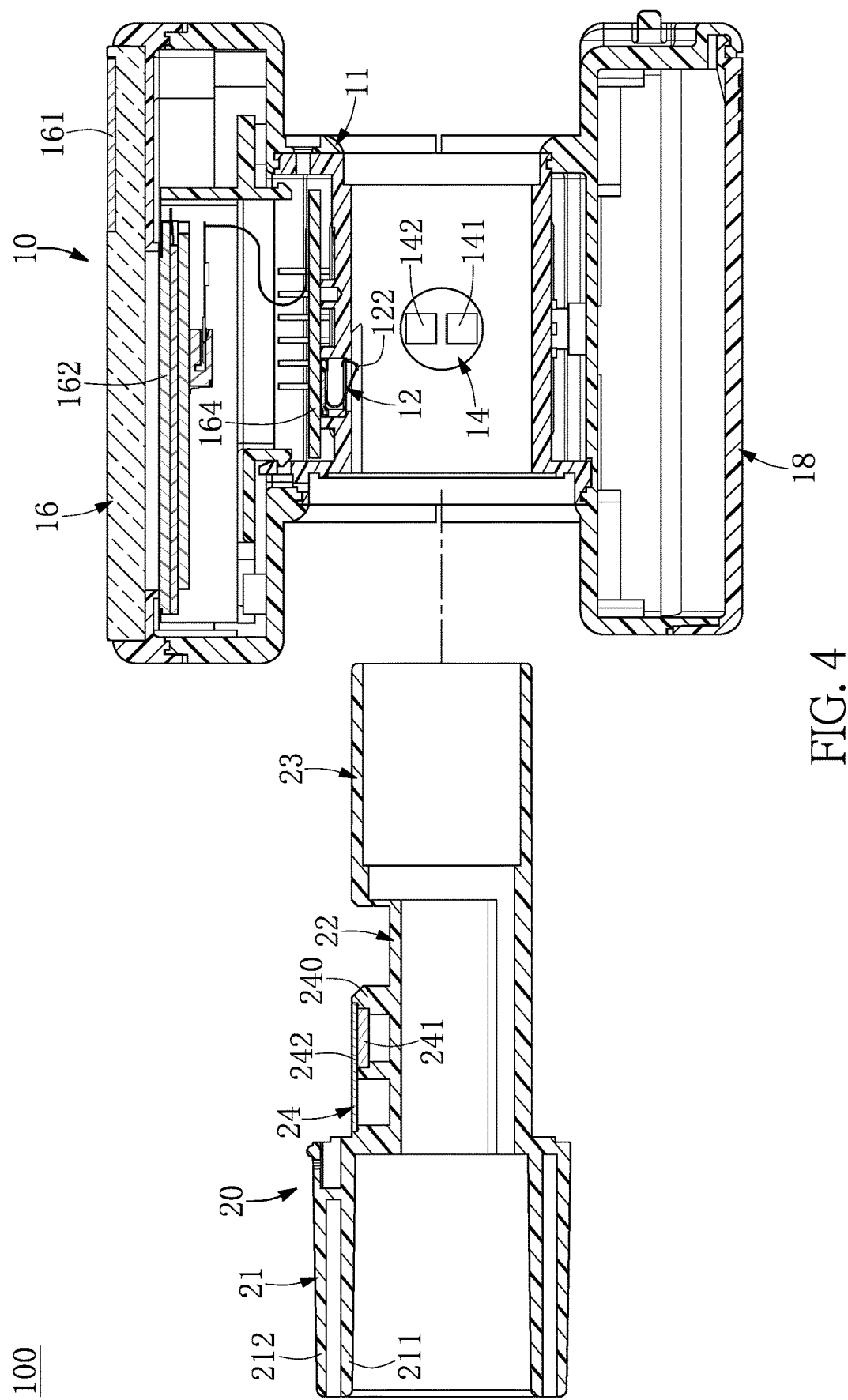
FIG. 4 is a cross-sectional view taken along line IV-IV of FIG. 1.

As shown in FIG. 1 and FIG. 4, the operation module 16 includes a membrane button 161, a display 162, and a micro controller unit (MCU) 164 that is disposed inside the operation module 16. The power supply module 18 can be powered by batteries to supply the required electrical energy.

The airway adapter 20 includes an inlet section 21, a detection section 22, an identification part 24 and an outlet section 23. As shown in FIG. 4, the inlet section 21 includes an inner pipe wall 211 and an outer pipe wall 212. The inner pipe wall 211 and the outer pipe wall 212 form a structure of concentric circles, which can be connected to a measurement pipe. The detection section 22 is integrally connected between the inlet section 21 and the outlet section 23. The detection section 22 includes a light entering detection window 221 and a light exiting detection window 222 that are integrally formed. The light entering detection window 221 and the light exiting detection window 222 are oppositely arranged on two sides of the detection section 22. The identification part 24 is disposed on one side of the detection section 22. The identification part 24 includes an identification chip 241. An outer diameter D21 of the inlet section 21 is greater than an outer diameter D23 of the outlet section 23.

Figure 3A:
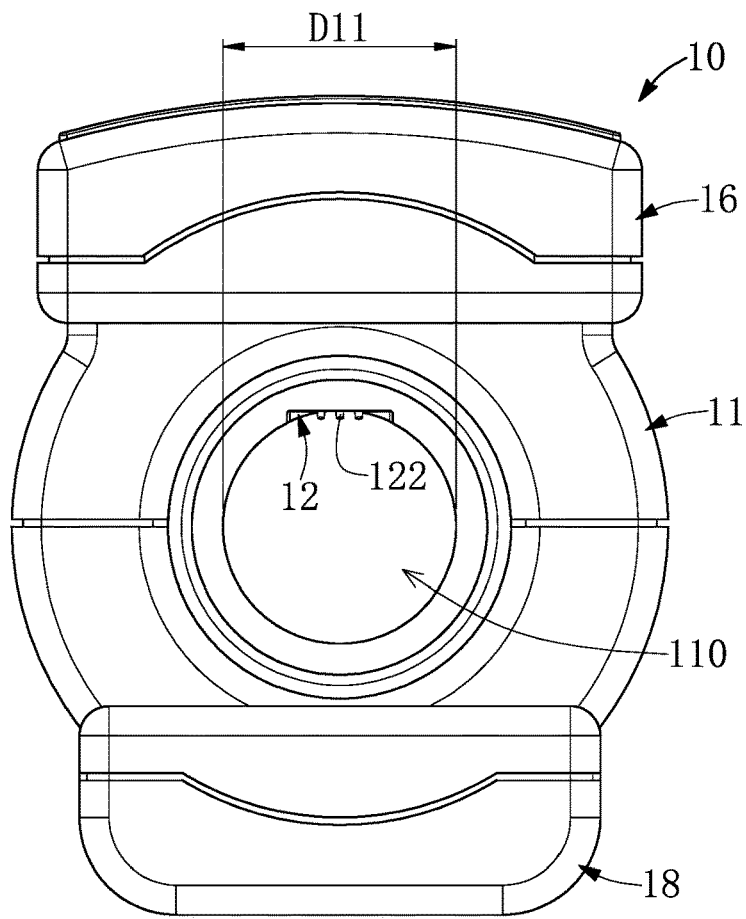
FIG. 3A is a front view of a gas concentration detection device according to the present disclosure.
Figure 3B:
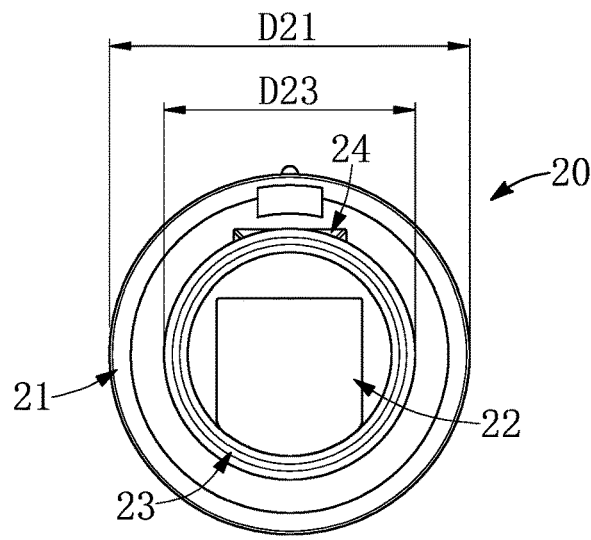
FIG. 3B is a front view of an airway adapter according to the present disclosure.

One of the features of the present embodiment is that, when the airway adapter 20 is mated with the accommodating passageway 110 of the gas concentration detection device 10, the outer diameter D23 of the outlet section 23 is equal to a diameter of the accommodating passageway D11 and is in tight contact with the circular outlet 110m of the accommodating passageway 110, and one end of the inlet section 21 abuts and covers the circular inlet 110n of the accommodating passageway 110 (as shown in FIG. 3). The airway adapter 20 is surrounded and completely covered by the main body 11 of the gas concentration detection device 10 (as shown in FIG. 6 to FIG. 9). In other words, the detection section 22 of the airway adapter 20 can be effectively protected from external light, especially infrared light.

Another feature of the present embodiment is that, when the airway adapter 20 is mated with the accommodating passageway 110 of the gas concentration detection device 10 (as shown in FIG. 6 to FIG. 9), the plurality of check terminals 122 abut the identification chip 241 of the identification part 24 to check whether or not the airway passageway 20 is matched with the gas concentration detection device 10, thereby preventing insertion of the wrong type of airway adapter into the gas concentration detection device. In addition, the identification chip 241 can be further used for writing or pre-storing digital information, such as characteristic data or personal data of the test subject. The identification chip 241 can be an electrically-erasable programmable read-only memory (EEPROM), but the present disclosure is not limited thereto.

Other features of the gas concentration measurement system 100 are described in more detail as follows. The check unit 12 in the present embodiment is recessed outwardly from an inner surface of the accommodating passageway 110, and is in a shape of a slightly squared groove. The identification part 24 is in a shape of a rectangular cube, which corresponds in shape to the squared groove of the check unit 12. As shown in FIG. 3, the identification part 24 partially protrudes from the outlet section 23 along an axial projection of the airway adapter 20, such that a guiding structure for preventing erroneous inserting is formed. In other words, a function of the check unit 12 in the present embodiment is to prevent erroneous insertion.

Figure 5:
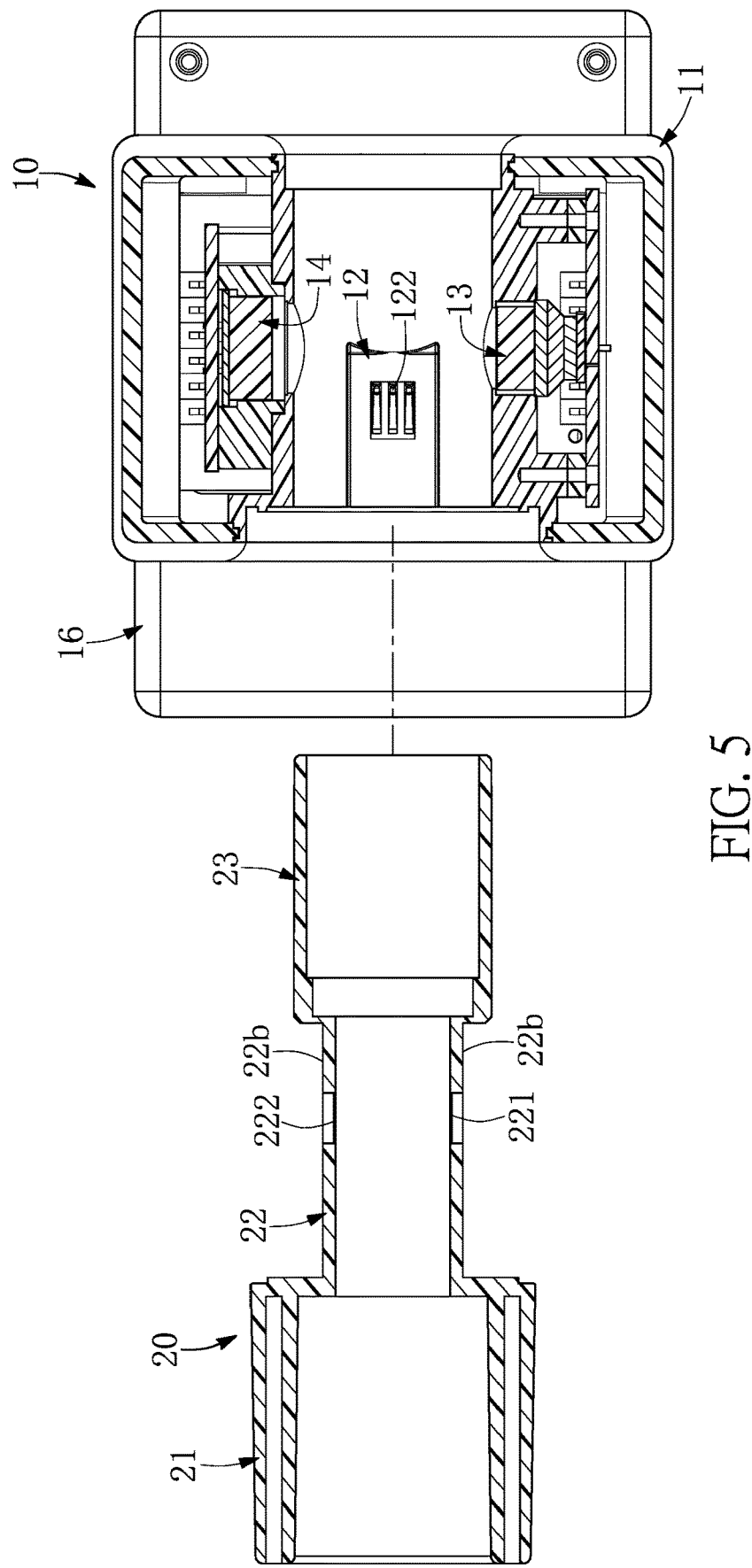
FIG. 5 is a cross-sectional view taken along line V-V of FIG. 1.
Figure 6:
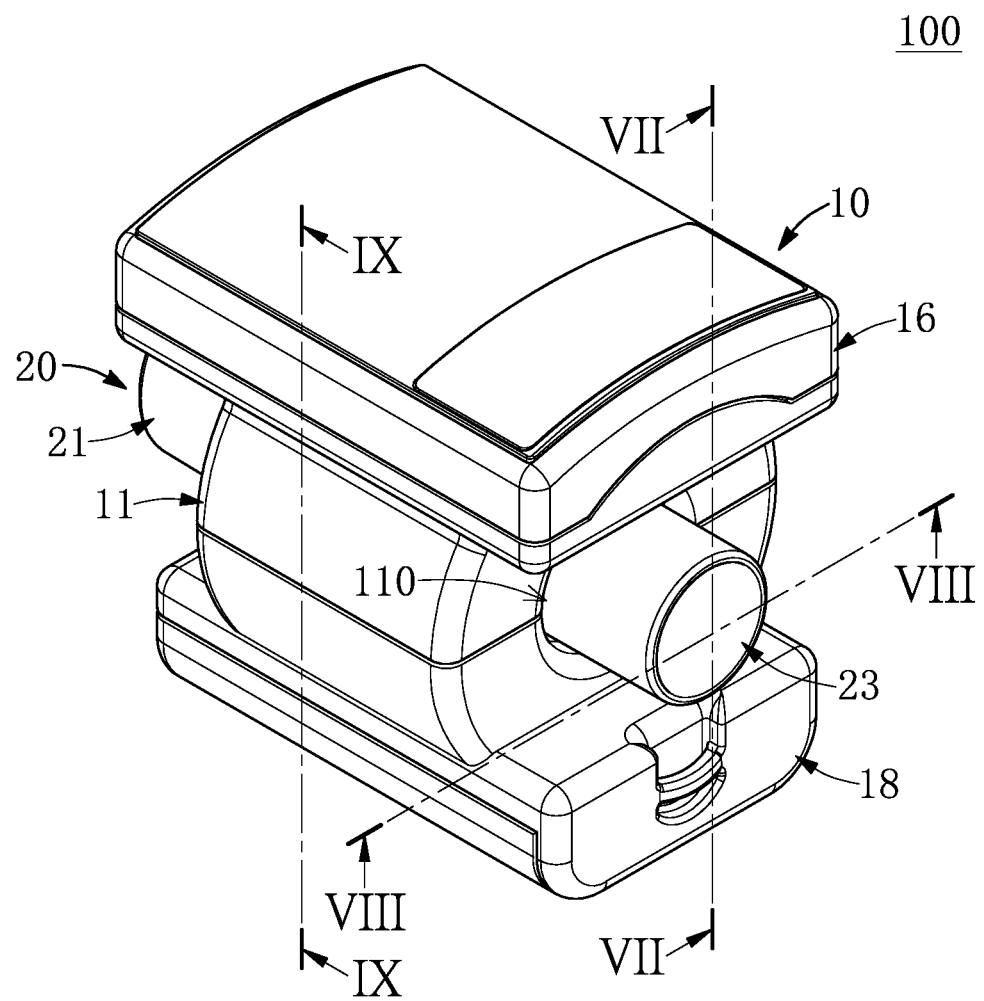
FIG. 6 is a perspective assembled view of the gas concentration measurement system according to the present disclosure.
Figure 7:
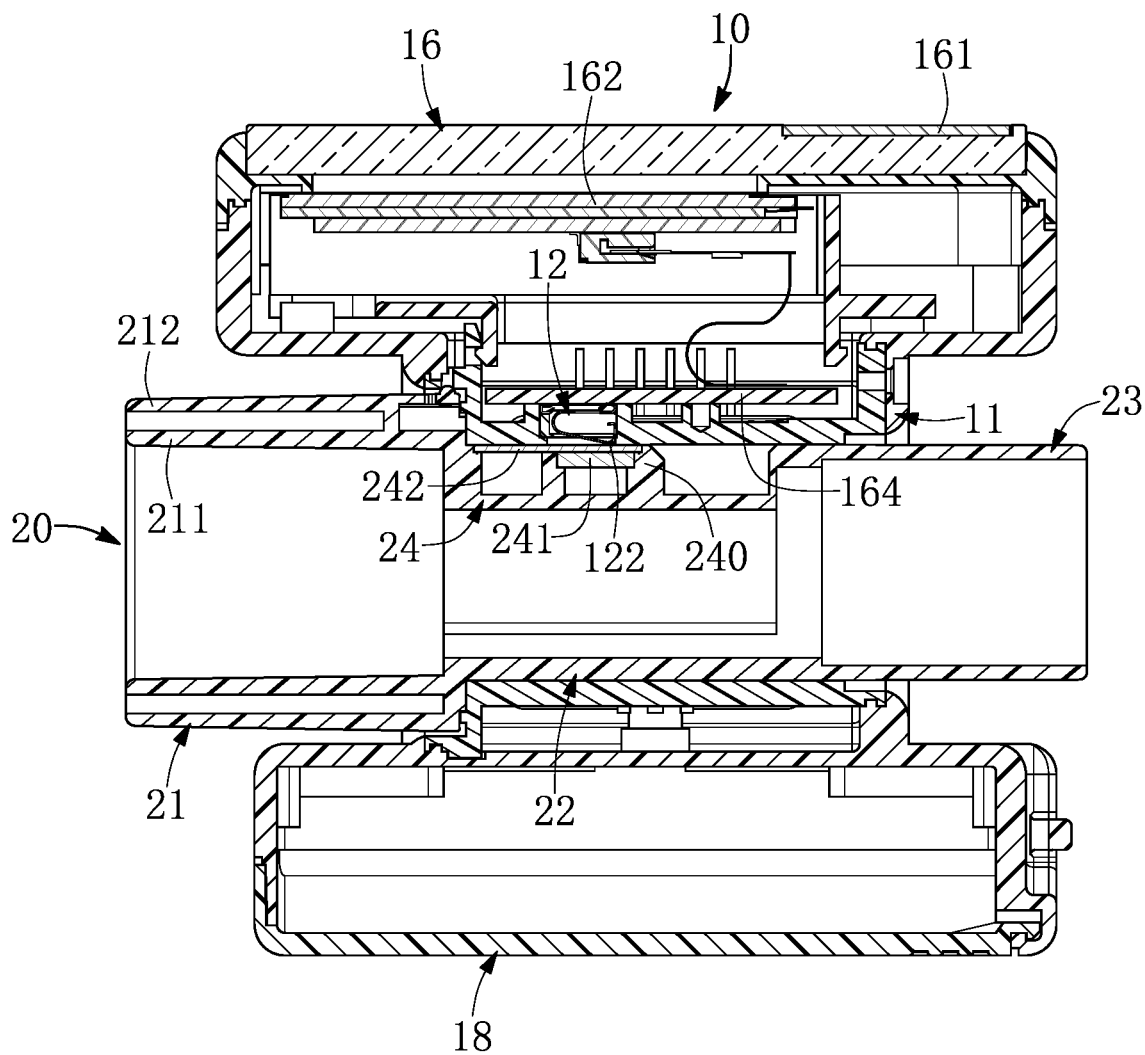
FIG. 7 is a cross-sectional view taken along line VII-VII of FIG. 6.
Figure 8:
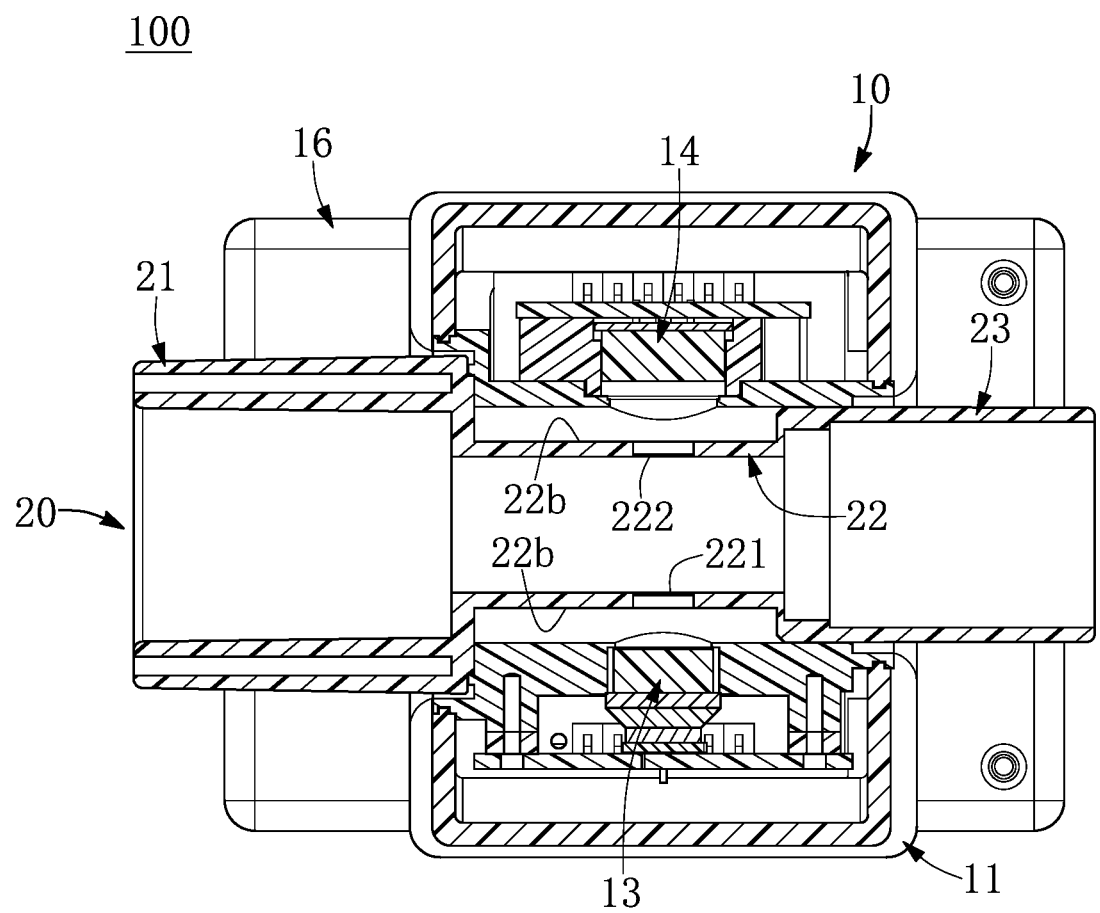
FIG. 8 is a cross-sectional view taken along line VIII-VIII of FIG. 6.
Figure 9:
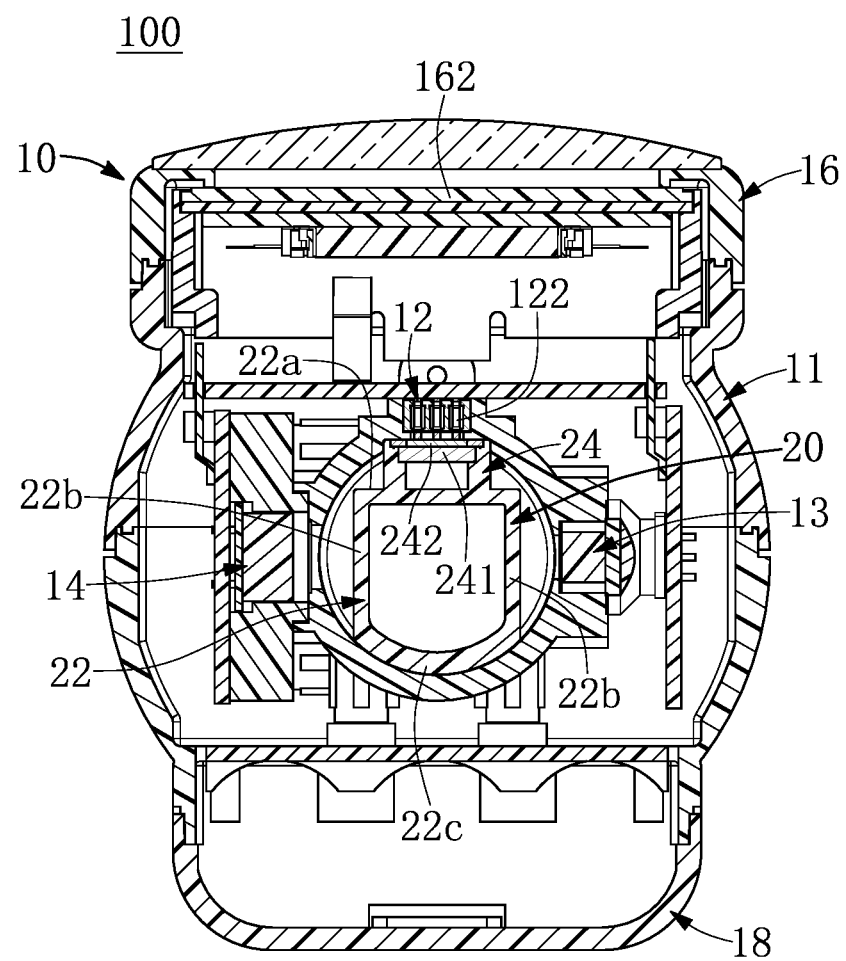
FIG. 9 is a cross-sectional view taken along line IX-IX of FIG. 6.

As shown in FIG. 1 and FIG. 5, the detection section 22 has a top wall 22a, a pair of side walls 22b and a bottom wall 22c. The pair of side walls 22b are parallel to each other and connected between the top wall 22a and the bottom wall 22c. A thickness of each of the light entering detection window 221 and the light exiting detection window 222 is less than a thickness of the side wall 22b of the detection section 22. In addition, in the present embodiment, the bottom wall 22c of the detection section 22 is arc-shaped and is flush with a surface of the outlet section 23.

As shown in FIG. 4, the identification part 24 includes a supporting casing 240 and a cover plate 242. The supporting casing 240 is integrally formed on the top wall 22a of the detection section 22. The identification chip 241 is housed in the supporting casing 240. The cover plate 242 covers the supporting casing 240. A part of the identification chip 241 is exposed outside an opening of the cover plate 242.

A further feature of the present embodiment is that the light entering detection window 221 and the light exiting detection window 222 are each coated with an anti-fog layer (thin and transparent, not shown in the drawing). The anti-fog layer can provide an anti-fog effect by way of an inner side of each of the light entering detection window 221 and the light exiting detection window 22 being coated with an anti-fog agent (such as a super-hydrophilic liquid). Accordingly, the air exhaled by the test subject is less likely to condense on a surface, and a measurement accuracy is improved.

One of the features of the airway adapter 20 in the present embodiment is that the light entering detection window 221 and the light exiting detection window 222 are integrally formed on the airway adapter 20 by injection molding. Steps of assembling the detection windows can be omitted from the present embodiment, and an assembling error that affects a measurement result can be prevented. In the present embodiment, the light entering detection window 221 and the light exiting detection window 222 are each 0.15 to 0.25 mm in thickness.

As shown in FIG. 4, the gas concentration measurement system in the present embodiment is a dual-beam, dual-wavelength measurement with two optical channels, which may improve accuracy and stability. The receiver unit 14 is composed of a first receiver 141 (as shown in FIG. 4) and a second receiver 142 (as shown in FIG. 4). The first receiver 141 has a filter for a first wavelength to receive a detection light of the first wavelength, and the second receiver 142 has a filter for a second wavelength to receive a detection light of the second wavelength. The first wavelength in the present embodiment is 4.26 μm, and $CO_2$ has a strongest absorption of infrared light from 4.26 μm to 4.3 μm. The second wavelength is 3.91 μm, which is less likely to be absorbed by $CO_2$ and can be used as a reference.

A measurement process of the gas concentration measurement system in the present embodiment is described as follows: the identification chip 241 of the airway adapter 20 is read by the check unit 12 of the gas concentration detection device 10 to determine whether or not the airway adapter 20 is inserted into the gas concentration detection device 10, and whether or not the inserted airway adapted 20 is a correct one.

The micro controller unit 164 of the operation module 16 enables the transmitter unit 13 to emit an infrared light at a fixed frequency through a light source control unit.

The infrared light at the fixed frequency passes through the airway adapter 20 through the light entering detection window 221.

The infrared light at the fixed frequency passes through two filter windows with respective wavelengths of 3.91 μm and 4.26 μm. That is, the infrared light at the fixed frequency is received by the first receiver 141 and the second receiver 142.

The light passing through the 3.91 μm filter and the 4.26 μm filter is converted into electrical signals $V_{CO2}$ and $V_{ref}$ through the first receiver 141 and the second receiver 142, respectively. After passing through a filtering and amplifying circuit, $V_{CO2}$ and $V_{ref}$ are converted into digital signals by an analog-to-digital converter (A/D converter), and then the digital signals of $V_{CO2}$ and $V_{ref}$ are back-calculated by the micro processing unit 164 to obtain a $CO_2$ concentration (including an altitude compensation) passing through the airway adapter 20. End tidal $CO_2$ ($EtCO_2$) and respiratory rate are then calculated from the back-calculated $CO_2$ concentration. Finally, an end tidal $CO_2$ value, the respiratory rate and a waveform are displayed through the display 162.

Beneficial Effects of the Embodiment

In conclusion, one of the beneficial effects of the present disclosure is that the gas concentration measurement system provided by the present disclosure can be mated with the accommodating passageway of the gas concentration detection device along the axis of the airway adapter, so that the detection section of the airway adapter can be completely surrounded and covered, thereby preventing the possible light interference and improving the measurement accuracy.

In addition, the gas concentration detection device includes the check unit, and the airway adapter includes the identification part. The plurality of check terminals of the check unit abut the identification chip of the identification part to check whether or not the airway adapter is matched with the gas concentration detection device.

The foregoing description of the exemplary embodiments of the disclosure has been presented only for the purposes of illustration and description and is not intended to be exhaustive or to limit the disclosure to the precise forms disclosed. Many modifications and variations are possible in light of the above teaching.

The embodiments were chosen and described in order to explain the principles of the disclosure and their practical application so as to enable others skilled in the art to utilize the disclosure and various embodiments and with various modifications as are suited to the particular use contemplated. Alternative embodiments will become apparent to those skilled in the art to which the present disclosure pertains without departing from its spirit and scope.

What is claimed is:

1. A gas concentration measurement system, comprising:
a gas concentration detection device including a main body, the main body including an accommodating passageway, a check unit, a transmitter unit and a receiver unit, the accommodating passageway being in a cylindrical shape and passing through the main body to form a circular inlet and a circular outlet, the transmitter unit and the receiver unit being oppositely disposed on two sides of the accommodating passageway, the check unit being disposed between the transmitter unit and the receiver unit, the check unit including a plurality of check terminals, the plurality of check terminals being exposed in the accommodating passageway; and an airway adapter including an inlet section, a detection section, an identification part and an outlet section, the detection section being integrally connected between the inlet section and the outlet section, the detection section including a light entering detection window and a light exiting detection window that are integrally formed, the light entering detection window and the light exiting detection window being oppositely arranged on two sides of the detection section, the identification part being disposed on one side of the detection section, the identification part having an identification chip disposed therein, an outer diameter of the inlet section being greater than an outer diameter of the outlet section;

wherein, when the airway adapter is mated with the accommodating passageway of the gas concentration detection device along an axis of the airway adapter, the plurality of check terminals abut the identification chip of the identification part to check whether or not the airway passageway is matched with the gas concentration detection device, the outer diameter of the outlet section is equal to a diameter of the accommodating passageway and is in tight contact with the circular outlet of the accommodating passageway, and one end of the inlet section abuts and covers the circular outlet of the accommodating passageway.

2. The gas concentration measurement system according to claim 1, wherein the gas concentration detection device further includes an operation module and a power supply module, and the operation module and the power supply module are arranged on two sides of the main body, respectively.

3. The gas concentration measurement system according to claim 1, wherein the inlet section has an inner pipe wall and an outer pipe wall, and the inner pipe wall and the outer pipe wall form a structure of concentric circles.

4. The gas concentration measurement system according to claim 1, wherein the check unit is recessed outwardly from an inner surface of the accommodating passageway, and the identification part partially protrudes from the outlet section along an axial projection of the airway adapter, such that a guiding structure for preventing erroneous insertion is formed.

5. The gas concentration measurement system according to claim 1, wherein the detection section has a top wall, a pair of side walls and a bottom wall, the pair of side walls being parallel to each other and connected between the top wall and the bottom wall, and a thickness of each of the light entering detection window and the light exiting detection window are less than a thickness of the side walls of the detection section.

6. The gas concentration measurement system according to claim 5, wherein the identification part includes a supporting casing and a cover plate, the supporting casing being integrally formed on the top wall of the detection section, the identification chip being housed in the supporting casing, the cover plate covering the supporting casing, and a part of the identification chip being exposed from the cover plate.

7. The gas concentration measurement system according to claim 1, wherein the light entering detection window and the light exiting detection window are each coated with an anti-fog layer.

8. The gas concentration measurement system according to claim 1, wherein a thickness of the light entering detection window and a thickness of the light exiting detection window are each from 0.15 to 0.25 mm.

9. The gas concentration measurement system according to claim 1, wherein the receiver unit is provided with a first receiver and a second receiver, the first receiver having a filter for a first wavelength to receive a detection light of the first wavelength, the second receiver having a filter for a second wavelength to receive a detection light of the second wavelength.

10. An airway adapter suitable for a gas concentration detection device of a gas concentration measurement system, the gas concentration detection device including a main body, the main body including an accommodating passageway, a check unit, a transmitter unit and a receiver unit, the transmitter unit and the receiver unit being oppositely disposed on two sides of the accommodating passageway, the check unit being disposed between the transmitter unit and the receiver unit, the check unit including a plurality of check terminals, the plurality of check terminals being exposed in the accommodating passageway, the accommodating passageway being in a cylindrical shape and passing through the main body to form a circular inlet and a circular outlet, the airway adapter comprising:

an inlet section, a detection section, an identification part and an outlet section, the detection section being integrally connected between the inlet section and the outlet section, the detection section including a light entering detection window and a light exiting detection window that are integrally formed, the light entering detection window and the light exiting detection window being oppositely arranged on two sides of the detection section, the identification part being disposed on one side of the detection section, the identification part having an identification chip disposed therein, an outer diameter of the inlet section being greater than an outer diameter of the outlet section;

wherein, when the airway adapter is mated with the accommodating passageway of the gas concentration detection device along an axis of the airway adapter, the plurality of check terminals abut the identification chip of the identification part to check whether or not the airway passageway is matched with the gas concentration detection device, the outer diameter of the outlet section is substantially equal to a diameter of the accommodating passageway and is in tight contact with the circular outlet of the accommodating passageway, and one end of the inlet section abuts and covers the circular outlet of the accommodating passageway.

11. The airway adapter according to claim 10, wherein the check unit is recessed outwardly from the inner surface of the accommodating passageway, and the identification part partially protrudes from the outlet section along an axial projection of the airway adapter, such a guiding structure for preventing erroneous inserting is formed.

12. The airway adapter according to claim 10, wherein the inlet section has an inner pipe wall and an outer pipe wall, and the inner pipe wall and the outer pipe wall form a structure of concentric circles.

13. The airway adapter according to claim 10, wherein the detection section has a top wall, a pair of side walls and a bottom wall, the pair of side walls being parallel to each other and connected between the top wall and the bottom wall, and a thickness of each of the light entering detection window and the light exiting detection window is less than a thickness of the side wall of the detection section.

14. The airway adapter according to claim 13, wherein the identification part includes a supporting casing and a cover plate, the supporting casing being integrally formed on the top wall of the detection section, the identification chip being housed in the supporting casing, the cover plate covering the supporting casing, and a part of the identification chip being exposed from the cover plate.

15. The airway adapter according to claim 10, wherein the light entering detection window and the light exiting detection window are each coated with an anti-fog layer.

16. The airway adapter according to claim 10, wherein a thickness of the light entering detection window and a thickness of the light exiting detection window are each from 0.15 to 0.25 mm.

* * * * *